(12) United States Patent
Fujiyoshi et al.

(10) Patent No.: US 10,729,393 B2
(45) Date of Patent: Aug. 4, 2020

(54) RADIOGRAPHIC IMAGING APPARATUS AND RADIOGRAPHIC IMAGING SYSTEM

(71) Applicant: CANON KABUSHIKI KAISHA, Tokyo (JP)

(72) Inventors: Kentaro Fujiyoshi, Tokyo (JP); Minoru Watanabe, Yokohama (JP); Keigo Yokoyama, Kawasaki (JP); Masato Ofuji, Takasaki (JP); Jun Kawanabe, Kawasaki (JP); Sho Sato, Tokyo (JP); Kazuya Furumoto, Tokyo (JP); Ryosuke Miura, Kawasaki (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 337 days.

(21) Appl. No.: 15/818,427

(22) Filed: Nov. 20, 2017

(65) Prior Publication Data

US 2018/0140264 A1 May 24, 2018

(30) Foreign Application Priority Data

Nov. 24, 2016 (JP) ................................. 2016-228061

(51) Int. Cl.
*A61B 6/00* (2006.01)
*H04N 5/32* (2006.01)
*G01T 1/24* (2006.01)

(52) U.S. Cl.
CPC ............ *A61B 6/4233* (2013.01); *A61B 6/54* (2013.01); *G01T 1/247* (2013.01); *H04N 5/32* (2013.01); *A61B 6/542* (2013.01)

(58) Field of Classification Search
None
See application file for complete search history.

(56) References Cited

U.S. PATENT DOCUMENTS

2013/0343522 A1* 12/2013 Yoon .................. G01T 1/17
378/62

FOREIGN PATENT DOCUMENTS

JP 2015-213221 A 11/2015

* cited by examiner

*Primary Examiner* — Hoon K Song
(74) *Attorney, Agent, or Firm* — Canon U.S.A., Inc. IP Division

(57) ABSTRACT

A radiographic imaging apparatus includes a pixel, a readout unit, and a signal processing unit. The pixel includes a switch configured to connect a conversion element configured to convert radiation into an electric signal to a signal line. The readout unit is configured to perform a first operation of reading out a first signal appearing in the signal line when the switch is not in a conductive state and a second operation of reading out a second signal appearing in the signal line when the switch is in a conductive state. The readout unit is configured to perform the first operation before performing the second operation a plurality of times consecutively. The signal processing unit is configured to perform signal processing for outputting information indicating irradiation of the radiographic imaging apparatus by the radiation based on the first signal and the second signal.

13 Claims, 14 Drawing Sheets

RADIOGRAPHIC IMAGING APPARATUS AND RADIOGRAPHIC IMAGING SYSTEM

BACKGROUND OF THE INVENTION

Field of the Invention

One disclosed aspect of the embodiments relates to a radiographic imaging apparatus and a radiographic imaging system.

Description of the Related Art

A radiographic imaging apparatus including an array formed by arraying pixels each including a combination of a switch such as a thin-film transistor (TFT) and a conversion element such as a photoelectric conversion element has been put into practical use as a radiographic imaging apparatus for use in a medical image diagnosis and a non-destructive inspection using radiation such as an X-ray. The switch is disposed between the conversion element and a column signal line, and a signal is read out from the conversion element via the column signal line by setting the switch into a conductive state. In recent years, equipping such a radiographic imaging apparatus with multiple functions has been considered. As one example thereof, incorporating an automatic exposure control (AEC) function has been considered. This function is used as means that allows the radiographic imaging apparatus to recognize irradiation information while the radiation source radiates the radiation rays. For example, this function can be used to recognize an incident start timing at which the radiation source radiates the radiation rays, recognize a stop timing at which the radiation is stopped, and recognize an irradiation amount and/or an integral irradiation amount of the radiation. Further, this function also allows the radiographic imaging apparatus to monitor the integral irradiation amount and control the radiation source to end the radiation when the integral irradiation amount reaches an appropriate amount.

A parasitic capacitance is generated between the column signal line for reading out the signal from the conversion element and electrodes of a plurality of conversion elements in a column where this column signal line is disposed in the array of the radiographic imaging apparatus. Due to this parasitic capacitance, the column signal line and the electrodes of the conversion elements may be capacitively coupled, and a crosstalk may occur. At the time of the automatic exposure control, the radiographic imaging apparatus needs to acquire the signal a plurality of times during the irradiation to recognize the irradiation amount during the irradiation. In a case where the signal is acquired during the irradiation, a potential of the column signal line may change due to the crosstalk because, when the signal is being read out from a conversion element of a pixel in some row via the column signal line, a potential of an electrode of a conversion element of a pixel in another row changes due to a photoelectric conversion. This change may cause a reduction in accuracy of the readout signal.

Japanese Patent Application Laid-Open No. 2015-213221 discusses a radiation detection apparatus that corrects the crosstalk to reduce the influence of the crosstalk. More specifically, the radiation detection apparatus repeats a first operation of reading out the signal without extracting the signal of the conversion element by blocking conduction of the switch element and a second operation of reading out the signal of the conversion element with the signal extracted from the conversion element by causing the switch element to be in a conductive state, and calculates a difference between them. In other words, in Japanese Patent Application Laid-Open No. 2015-213221, the radiation detection apparatus acquires a signal amount of the radiation by repeating sampling twice by a pair of the first operation and the second operation when correcting the crosstalk.

However, in Japanese Patent Application Laid-Open No. 2015-213221, the radiation detection apparatus takes a time corresponding to approximately twice an interval of sampling the signal of the conversion element to acquire the signal, and therefore leaves room for improvement in terms of a temporal resolution. The detection of the irradiation amount for the AEC requires the signal to be acquired the plurality of times in a time period as short as during the irradiation, so that the reduction in the temporal resolution leads to a larger change in an increase in the irradiation amount, making it difficult to recognize a small amount of increase. Therefore, this apparatus may have difficulty in stopping the radiation when an optimum irradiation time period has elapsed.

SUMMARY OF THE INVENTION

One disclosed aspect of the embodiments is directed to a technique advantageous for reducing the influence of the crosstalk without reducing the temporal resolution in the radiographic imaging apparatus that acquires the signal to recognize the irradiation amount during the irradiation. According to an aspect of the embodiments, a radiographic imaging apparatus includes a pixel, a readout unit, and a signal processing unit. The pixel includes a conversion element configured to convert radiation into an electric signal and a switch configured to connect the conversion element to a signal line. The readout unit is configured to perform a first operation of reading out a first signal appearing in the signal line when the switch is not in a conductive state and a second operation of reading out a second signal appearing in the signal line when the switch is in a conductive state during a time period when the radiographic imaging apparatus is irradiated with the radiation. The read out unit is also configured to perform the first operation before performing the second operation a plurality of times consecutively. The signal processing unit is configured to perform signal processing for outputting information indicating irradiation of the radiographic imaging apparatus with the radiation based on the first signal and the second signal.

Further features of the disclosure will become apparent from the following description of exemplary embodiments with reference to the attached drawings.

DESCRIPTION OF THE EMBODIMENTS

In the following description, the disclosure will be described through exemplary embodiments thereof with reference to the accompanying drawings.

Figure 1:
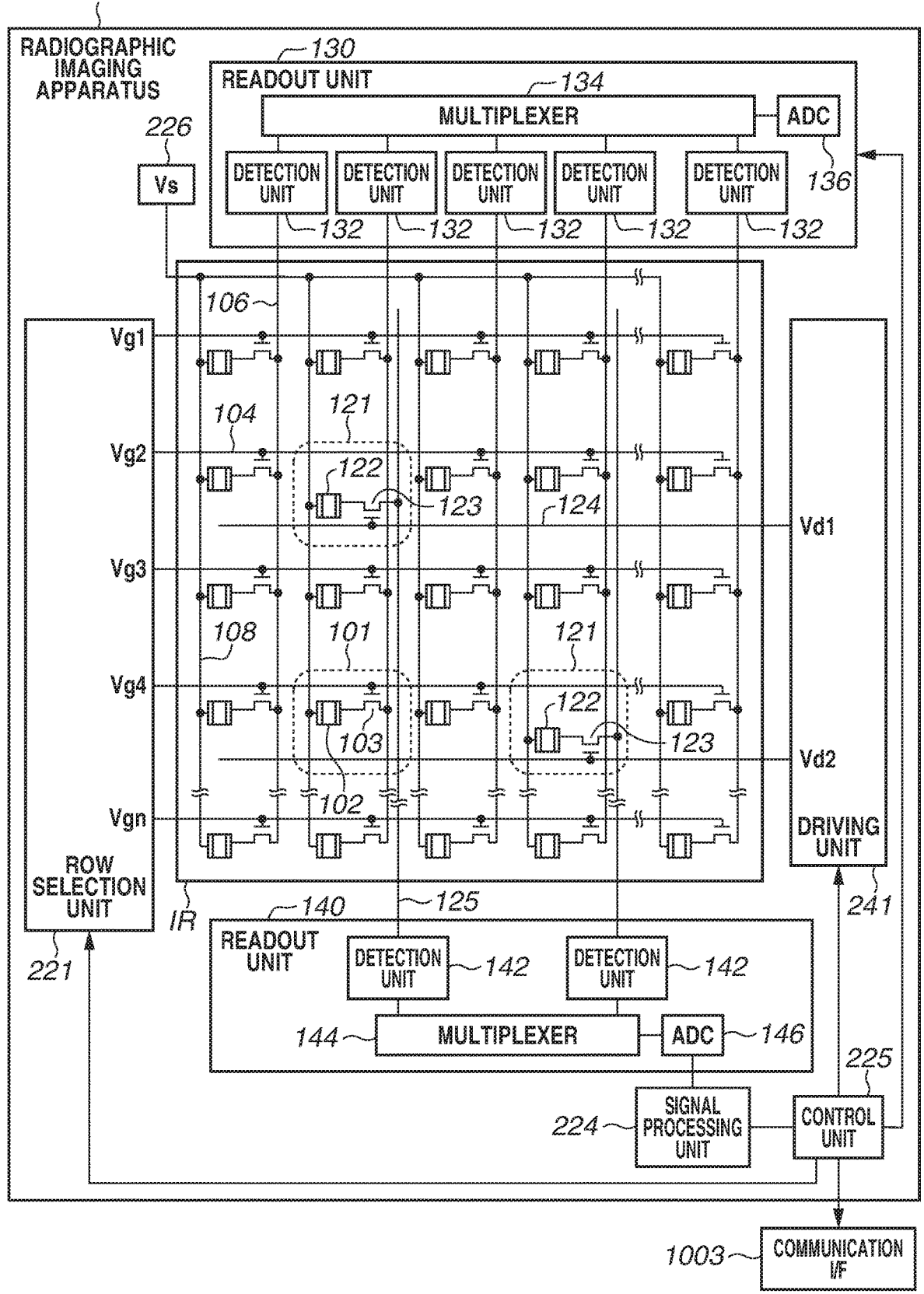
FIG. 1 is a diagram illustrating a configuration of a radiographic imaging apparatus according to a first exemplary embodiment.

FIG. 1 illustrates a configuration of a radiographic imaging apparatus 200 according to a first exemplary embodiment. The radiographic imaging apparatus 200 includes a plurality of pixels arranged in an imaging region IR so as to form a plurality of rows and a plurality of columns. This plurality of pixels includes a plurality of imaging pixels 101 for acquiring a radiographic image, and a detection pixel 121 for monitoring irradiation by radiation. For example, the radiographic image may reflect an image of a part of a subject to which the irradiation is directed. The imaging pixels 101 each include a first conversion element 102, which converts the radiation into an electric signal, and a first switch 103, which is disposed between a column signal line 106 and the first conversion element 102. The detection pixel 121 includes a second conversion element 122, which converts the radiation into an electric signal, and a second switch 123, which is disposed between a detection signal line 125 and the second conversion element 122. The detection pixel 121 can be disposed in the same column as a part of the plurality of imaging pixels 101.

The first conversion element 102 and the second conversion element 122 can each include a scintillator that converts the radiation into light, and a photoelectric conversion element that converts the light into the electric signal. Generally, the scintillator can be formed into a sheet-like shape so as to cover the imaging region IR, and be shared by a plurality of pixels. Alternatively, the first conversion element 102 and the second conversion element 122 can each include a conversion element that directly converts the radiation into the electric signal.

The first switch 103 and the second switch 123 can each include a thin-film transistor (TFT) having an active region made from a semiconductor such as amorphous silicon or polycrystalline silicon (desirably, polycrystalline silicon).

The radiographic imaging apparatus 200 includes a plurality of column signal lines 106 and a plurality of driving lines 104. Each of the column signal lines 106 corresponds to one of the plurality of columns in the imaging region IR. Each of the driving lines 104 corresponds to one of the plurality of rows in the imaging region IR. Each of the driving lines 104 is driven by a row selection unit 221.

A first electrode of the first conversion element 102 is connected to a first main electrode of the first switch 103, and a second electrode of the first conversion element 102 is connected to a bias line 108. Then, one bias line 108 extends in a column direction, and is connected in common to the second electrodes of the plurality of conversion elements 102 arranged in the column direction. The bias line 108 receives a bias voltage Vs from a power source circuit 226. Second main electrodes of the first switches 103 of the plurality of imaging pixels 101 forming one column are connected to one column signal line 106. Control electrodes of the first switches 103 of the plurality of imaging pixels 101 forming one row are connected to one driving line 104.

The plurality of column signal lines 106 is connected to a readout unit or readout circuit 130. The readout unit 130 can include a plurality of detection units (or circuits) 132, a multiplexer 134, and an analog-to-digital converter (hereinafter referred to as an AD converter) 136. Each of the plurality of column signal lines 106 is connected to a detection unit (or circuit) 132 corresponding thereto among the plurality of detection units 132 of the readout unit 130. One column signal line 106 corresponds to one detection unit 132. The detection unit 132 includes, for example, a differential amplifier. The multiplexer 134 selects the plurality of detection units 132 in a predetermined order, and supplies a signal from the selected detection unit 132 to the AD converter 136. The AD converter 136 converts the supplied signal into a digital signal and outputs the converted signal.

A first electrode of the second conversion element 122 is connected to a first main electrode of the second switch 123, and a second electrode of the second conversion element 122 is connected to the bias line 108. A second main electrode of the second switch 123 is connected to the detection signal line 125. A control electrode of the second switch 123 is electrically connected to the driving line 124. The radiographic imaging apparatus 200 can include a plurality of detection signal lines 125. One or more detection pixel(s) 121 can be connected to one detection signal line 125. The driving line 124 is driven by a driving unit (or circuit) 241. One or more detection pixel(s) 121 can be connected to one driving line 124.

The detection signal line 125 is connected to a readout unit 140. Then, the readout unit 140 can include a plurality of detection units 142, a multiplexer 144, and an AD converter 146. Each of the plurality of detection signal lines 125 can be connected to a detection unit 142 corresponding thereto among the plurality of detection units 142 of the readout unit 140. Then, one detection signal line 125 corresponds to one detection unit 142. The detection unit 142 includes, for example, a differential amplifier. The multiplexer 144 selects the plurality of detection units 142 in a predetermined order, and supplies a signal from the selected detection unit 142 to the AD converter 146. The AD converter 146 converts the supplied signal into a digital signal and outputs the converted signal.

An output of the readout unit 140 (the AD converter 146) is supplied to a signal processing unit 224 and processed by the signal processing unit 224. The signal processing unit 224 outputs information indicating the irradiation of the radiographic imaging apparatus 200 by the radiation based on the output of the readout unit 140 (the AD converter 146). The information may represent, describe, or specify the irradiation either quantitatively or qualitatively. More specifically, the signal processing unit 224, for example, detects the irradiation of an irradiation area in the radiographic imaging apparatus 200 by the radiation, and calculates an irradiation amount and/or an integral irradiation amount of the radiation. The irradiation area may be an area corresponding to a region or area, of a subject, where the radiation is aimed at. A control unit 225 controls the row selection unit 221, the driving unit 241, and the readout unit 130 based on the information from the signal processing unit 224. The control unit 225 controls, for example, a start and an end of an exposure (an accumulation of a charge corresponding to the radiation with which an irradiation area of the radiographic imaging apparatus 200 is irradiated that is accumulated by the imaging pixel 101) based on the information from the signal processing unit 224.

Figure 2:
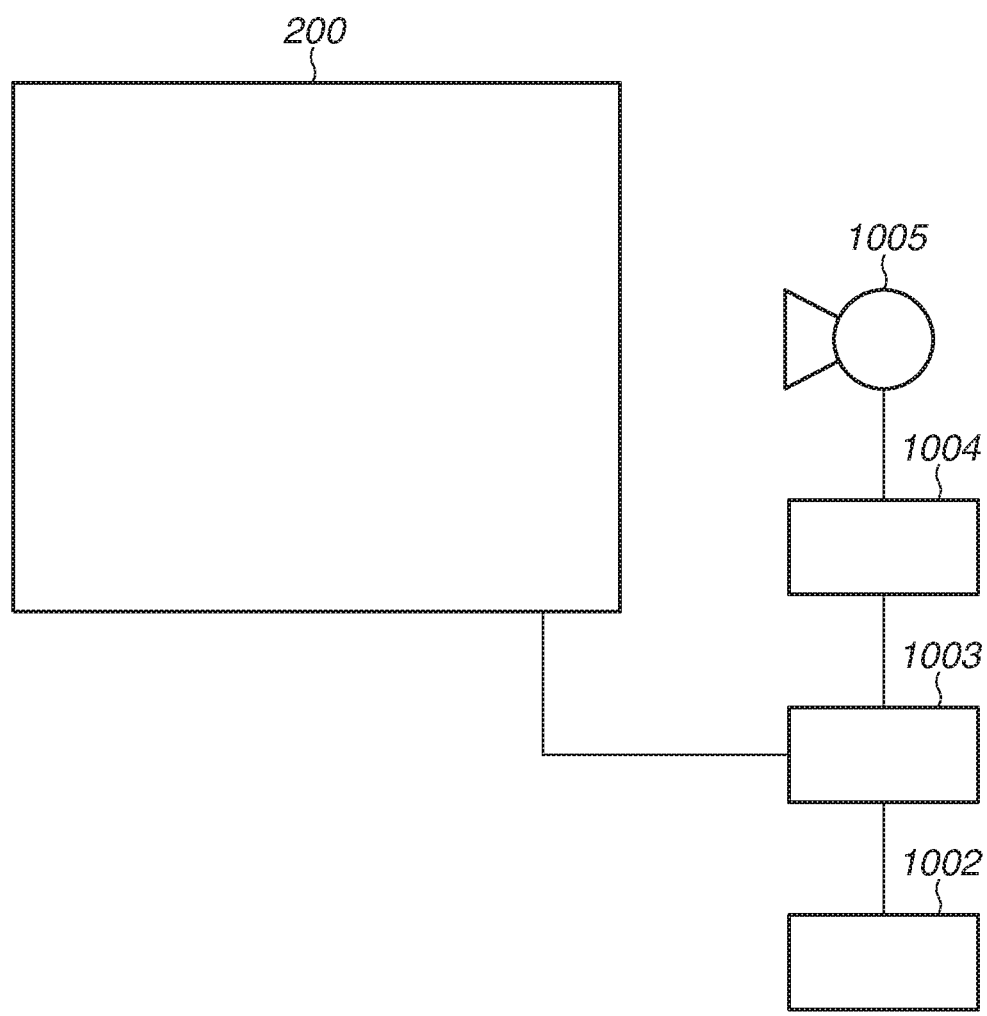
FIG. 2 is a block diagram illustrating an example of a configuration of a radiographic imaging system including the radiographic imaging apparatus.

FIG. 2 illustrates an example of a configuration of a radiographic imaging system including the radiographic imaging apparatus 200. The radiographic imaging system includes a controller 1002, an interface 1003, a radiation source interface 1004, and a radiation source 1005, besides the radiographic imaging apparatus 200.

A dose A, an irradiation time period B (ms), an X-ray tube current C (mA), an X-ray tube voltage D (kV), a radiation detection region (a region of interest (ROI)), which is a region where the radiation should be monitored, and the like can be input to the controller 1002. When an exposure switch attached to the radiation source 1005 is operated, the radiation is emitted from the radiation source 1005. The control unit 225 of the radiographic imaging apparatus 200 transmits an exposure stop signal to the radiation source interface 1004 via the interface 1003 when, for example, an integral value of the signal read out from the detection pixel 121 disposed in the radiation detection region (ROI) reaches a dose A'. In response thereto, the radiation source interface 1004 causes the radiation source 1005 to stop emitting the radiation. The dose A' can be determined by the control unit 225 based on the dose A, an intensity of the irradiation, a communication delay between individual units, a processing delay, and the like. If an irradiation time period of the radiation reaches the irradiation time period B, the radiation source 1005 stops the radiation regardless of whether the exposure stop signal is issued.

In the first exemplary embodiment, the radiographic imaging system cannot read out image information of a portion where the detection pixel 121 is located, but can acquire the information of the portion where the detection pixel 121 is located by performing interpolation processing with use of the output of the imaging pixels 101 around the detection pixel 121.

Figure 3:
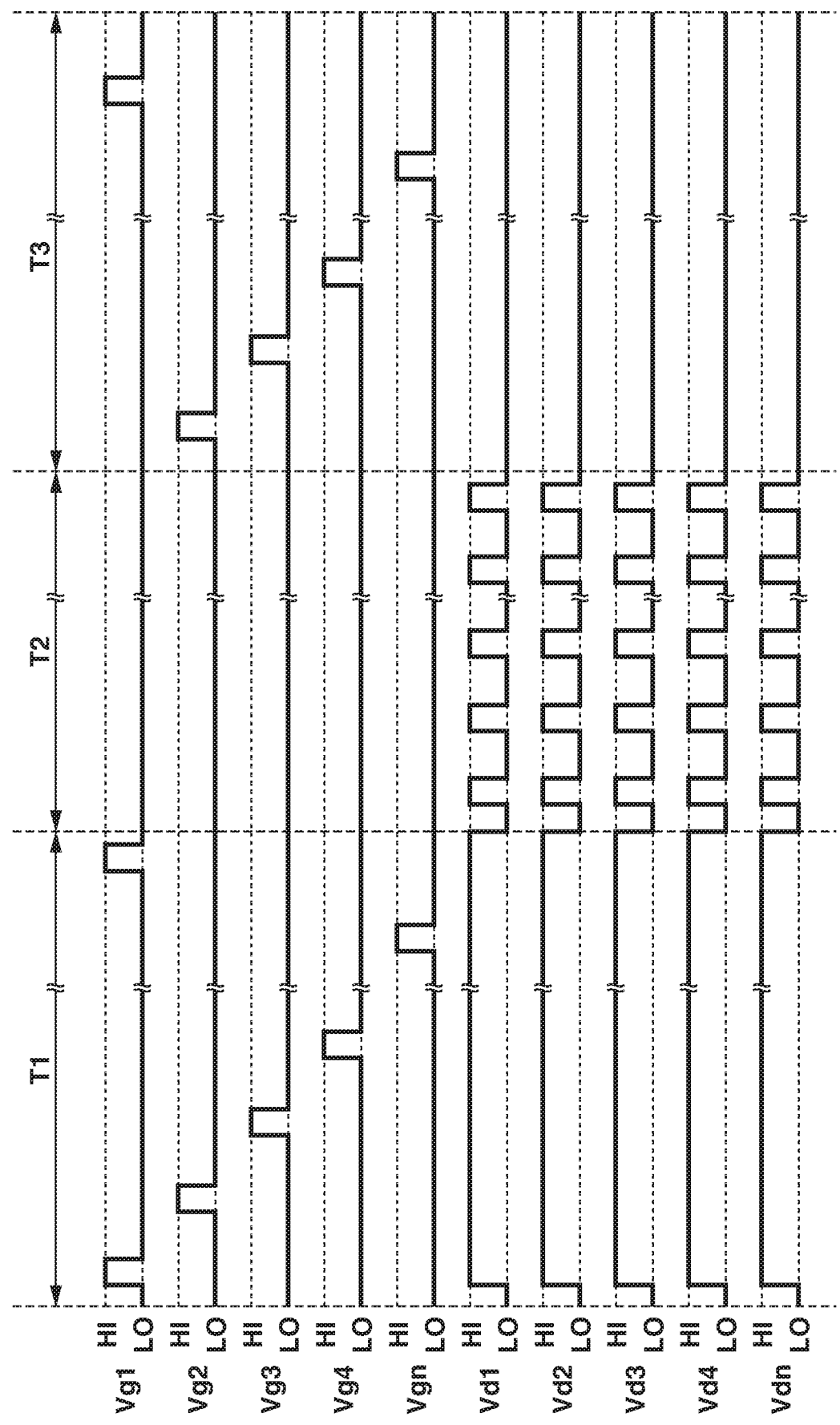
FIG. 3 is a timing chart illustrating an operation of the radiographic imaging apparatus according to the first exemplary embodiment.

FIG. 3 illustrates an example of an operation of the radiographic imaging apparatus 200 according to the first exemplary embodiment. In the following description, assume that Vg1 to Vgn each represent the signal applied to the driving line 104, which drives the imaging pixel 101, and Vd1 to Vdn each represent the signal applied to the driving line 124, which drives the detection pixel 121. The first switch 103 and the second switch 123 are caused to be in a conductive state when a signal supplied to a gate is at a high level, and into a non-conductive state when the signal supplied to the gate is at a low level.

A time period T1 is a time period during which the radiographic imaging apparatus 200 is waiting for a start of the irradiation by the radiation. More specifically, the time period T1 is a time period since the radiographic imaging apparatus 200 is powered on and is set into a state ready for capturing the radiographic image until the exposure switch of the radiation source 1005 is operated and the irradiation by the radiation is detected.

During the time period T1, Vd1 to Vdn are fixed at the high level, and the second switch 123 of the detection pixel 121 is fixed in the conductive state. The signal read out from the detection pixel 121 by the readout unit 140 is processed by the signal processing unit 224, and the start of the irradiation by the radiation is detected. When the start of the irradiation by the radiation is detected, the radiographic imaging apparatus 200 transitions to a time period T2. In the time period T1, it is desirable to periodically reset the first conversion element 102 of each of the imaging pixels 101 to a constant potential to remove a dark current generated in the conversion element 102. In this example, the voltages Vg1 to Vgn of the individual driving lines 104 are each switched to the high level sequentially, and the conversion element 102 is electrically connected to the column signal line 106 fixed at the constant potential. By this operation, a charge due to the dark current is prevented from being accumulated in the conversion element 102 over a long time period. A length of the time period T1 differs considerably depending on an imaging method, an imaging condition, and the like, but can be, for example, from several seconds to several minutes.

The time period T2 is a time period during which the radiographic imaging apparatus 200 is irradiated with the radiation. As one example, the time period T2 is a time period from the start of the irradiation by the radiation is detected until an exposure amount of the radiation reaches an optimum dose. The time period T2 can also be said to be a time period during which the irradiation amount of the radiation is monitored. During the time period T2, Vd1 to Vdn are intermittently switched to the high level, and the second switch 123 of the detection pixel 121 is intermittently caused to be in the conductive state.

The signal read out from the detection pixel 121 by the readout unit 140 is processed by the signal processing unit 224, and the dose is detected. During the time period T2, the signals Vg1 to Vgn applied to the individual driving lines 104 are each switched to the low level. By this operation, the generated charge is accumulated in the first conversion element 102 of the imaging pixel 101. A length of the time period T2 considerably differs depending on the imaging method, the imaging condition, and the like, but can be, for example, from approximately 1 millisecond to several hundred seconds.

The control unit 225 causes the operation of the radiographic imaging apparatus 200 to transition to a time period T3 when the integral value of the signal read out from the detection pixel 121 disposed in the radiation detection region (ROI) reaches the dose A'. Further, at this time, the control unit 225 transmits the exposure stop signal to the radiation source interface 1004 via the interface 1003.

A time period T3 is a time period during which the signal accumulated in the imaging pixel 101 due to the radiation is read out after the irradiation by the radiation is ended. During the time period T3, Vd1 to Vdn are switched to the low level. In the time period T3, it is desirable to connect the detection signal line 125 to a fixed potential to prevent the detection signal line 125 from floating.

During the time period T3, Vg1 to Vgn are switched to the high level sequentially to scan a plurality of rows. The signal accumulated in the imaging pixel 101 is read out by the readout unit 140. In the present example, a row to which the high level is applied first is determined according to a row to which the high level is applied last in the time period T1 in such a manner that the accumulation time period is kept constant among the individual imaging pixels 101. In FIG. 3, the row to which the high level is applied last in the time period T1 is the row corresponding to Vg1, so that the high level is applied starting from a row corresponding to Vg2 sequentially in the time period T3.

Figure 4:
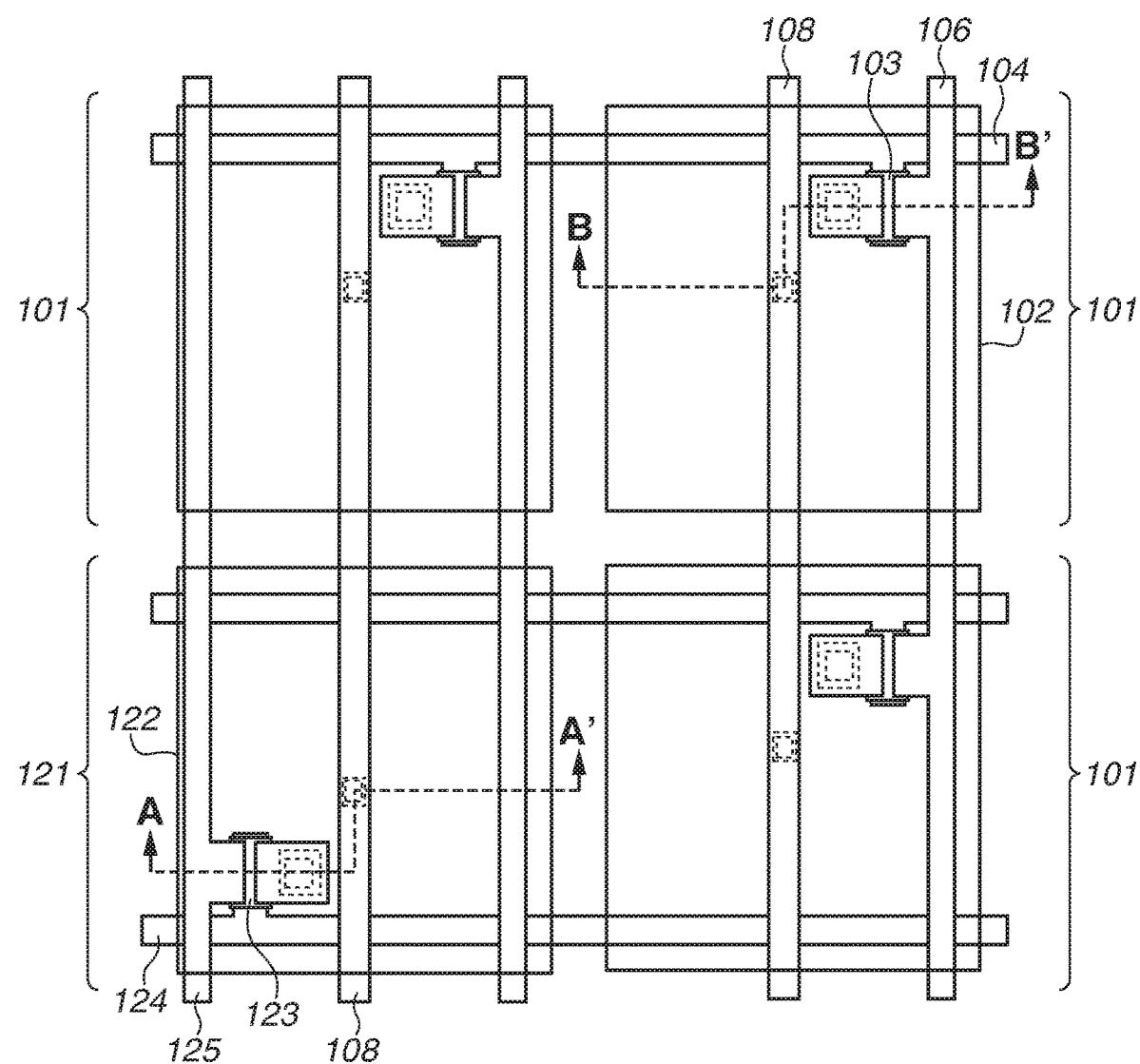
FIG. 4 is a plan view illustrating configurations of an imaging pixel and a detection pixel in the radiographic imaging apparatus according to the first exemplary embodiment.
Figure 5A:
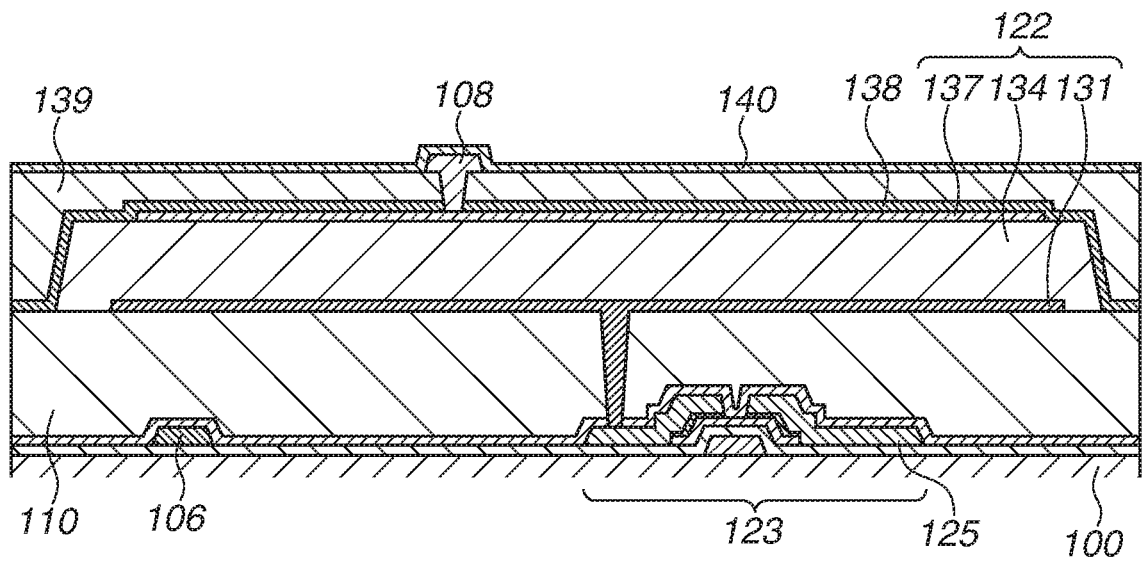
FIG. 5A is a cross-sectional view taken along a line A-A' illustrated in FIG. 4.

FIG. 4 is a plan view illustrating configurations of the imaging pixel 101 and the detection pixel 121 in the radiographic imaging apparatus 200 according to the first exemplary embodiment. The plan view is equivalent to an orthogonal projection onto a plane in parallel with the imaging region IR of the radiographic imaging apparatus 200. FIG. 5A is a cross-sectional view taken along a line A-A' illustrated in FIG. 4, and FIG. 5B is a cross-sectional view taken along a line B-B' illustrated in FIG. 4.

As exemplified in FIGS. 4 and 5A, the detection pixel 121 includes the second conversion element 122 and the second switch 123. In the present example, the second conversion element 122 converts the light converted from the radiation by the not-illustrated scintillator into the charge and accumulates the converted charge. However, the second conversion element 122 may be configured to directly convert the radiation into the charge. The second switch 123 includes the TFT that outputs the electric signal according to the charge accumulated in the second conversion element 122. The second conversion element 122 can be, for example, a positive-intrinsic-negative (PIN) type photodiode 134. The second conversion element 122 is connected to the detection signal line 125 via the second switch 123. The second conversion element 122 can be disposed on the second switch 123 disposed on an insulating support substrate 100 such as a glass substrate with an interlayer insulation layer 110 inserted between the second conversion element 122 and the second switch 123. The second conversion element 122 can include, for example, a first electrode 131, the PIN photodiode 134, and a second electrode 137.

A protective film 138, a second interlayer insulation layer 139, the bias line 108, and a protective film 140 are disposed on the second conversion element 122 in order. A not-illustrated planarization film and scintillator are disposed on the protective film 140. The second electrode 137 is connected to the bias line 108 via a contact hole. Light transmissive indium tin oxide (ITO) is used as the second electrode 137, and the second electrode 137 is configured to allow the light converted from the radiation by the not-illustrated scintillator to be transmitted therethrough.

Figure 5B:
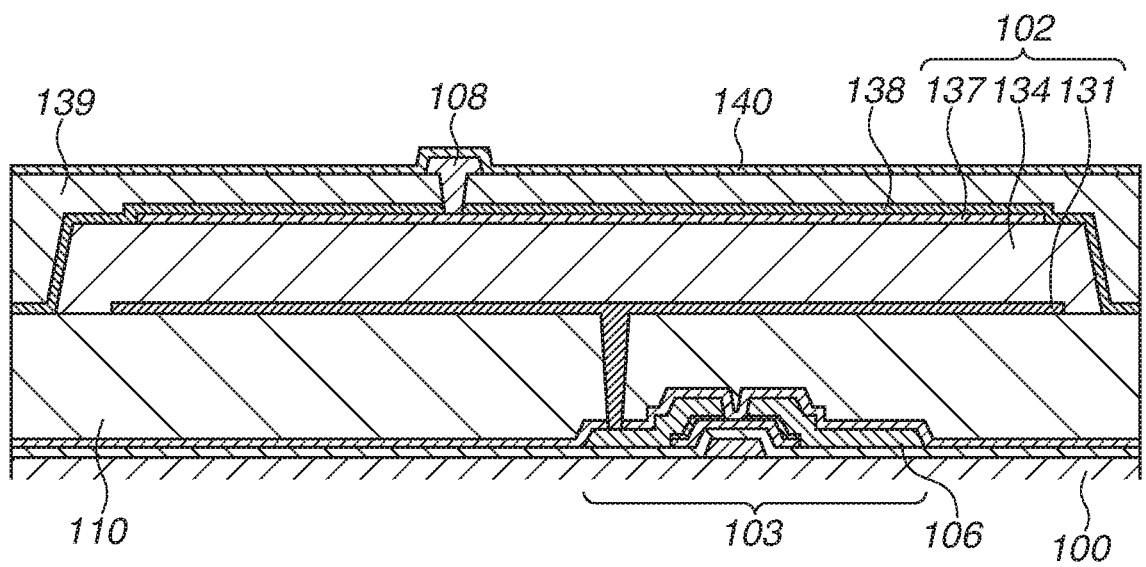
FIG. 5B is a cross-sectional view taken along a line B-B' illustrated in FIG. 4.

As exemplified in FIGS. 4 and 5B, the imaging pixel 101 includes the first conversion element 102 and the first switch 103. The first conversion element 102 converts the light converted from the radiation by the not-illustrated scintillator into the charge and accumulates the converted charge similarly to the second conversion element 122. However, the first conversion element 102 may be configured to directly convert the radiation into the charge. The first switch 103 includes the TFT that outputs the electric signal according to the charge accumulated in the first conversion element 102. The first conversion element 102 can be, for example, the PIN-type photodiode 134. The first conversion element 102 is connected to the column signal line 106 via the first switch 103. The first conversion element 102 can be disposed on the first switch 103 disposed on the insulating support substrate 100 such as the glass substrate with the interlayer insulation layer 110 inserted between the first conversion element 102 and the first switch 103. The first conversion element 102 can include, for example, the first electrode 131, the PIN-type photodiode 134, and the second electrode 137. The first conversion element 102 and the second conversion element 122 may be constructed with use of, for example, a metal-insulator-semiconductor (MIS) type sensor.

Figure 6:
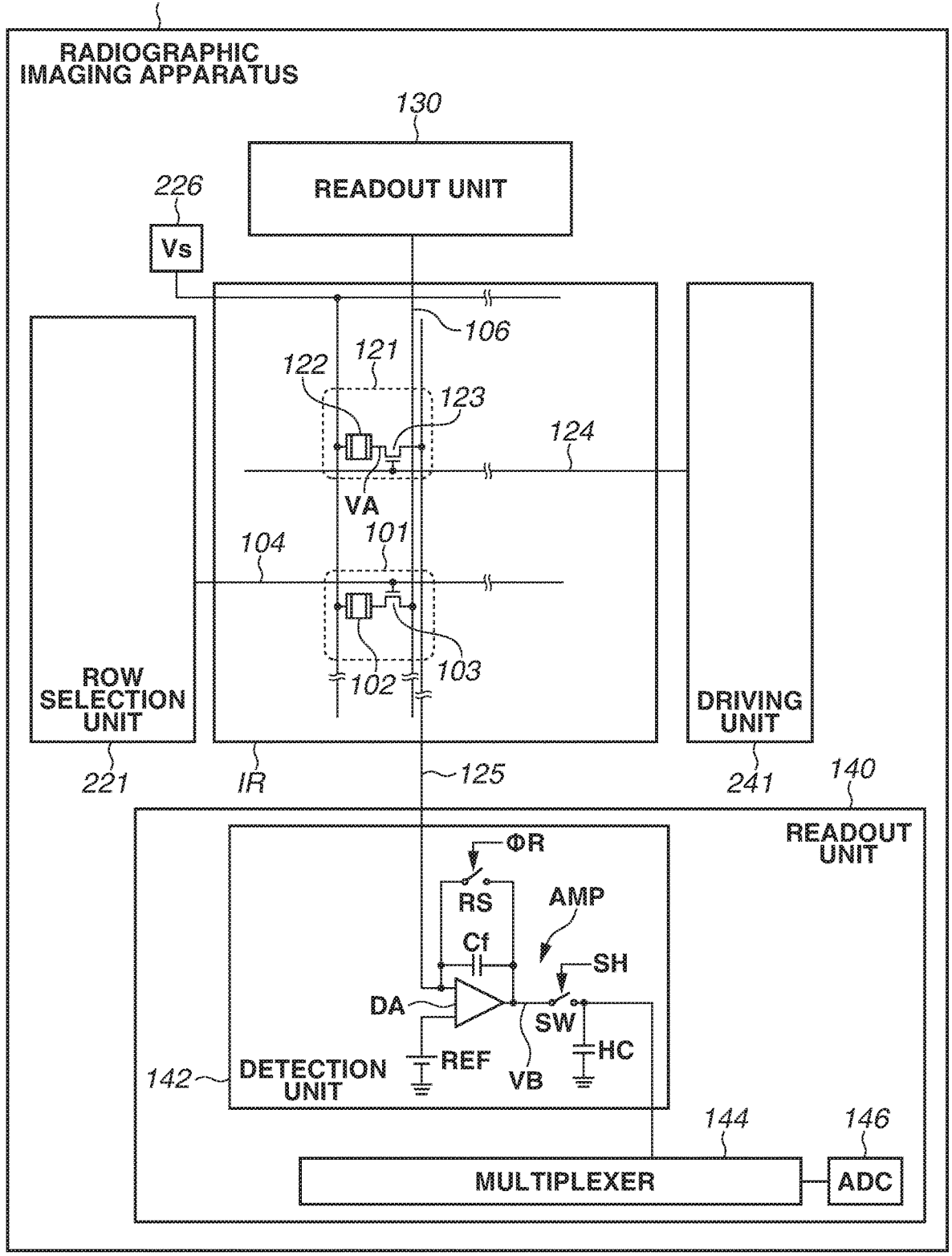
FIG. 6 is a diagram illustrating the configuration of the radiographic imaging apparatus according to the first exemplary embodiment.
Figure 7:
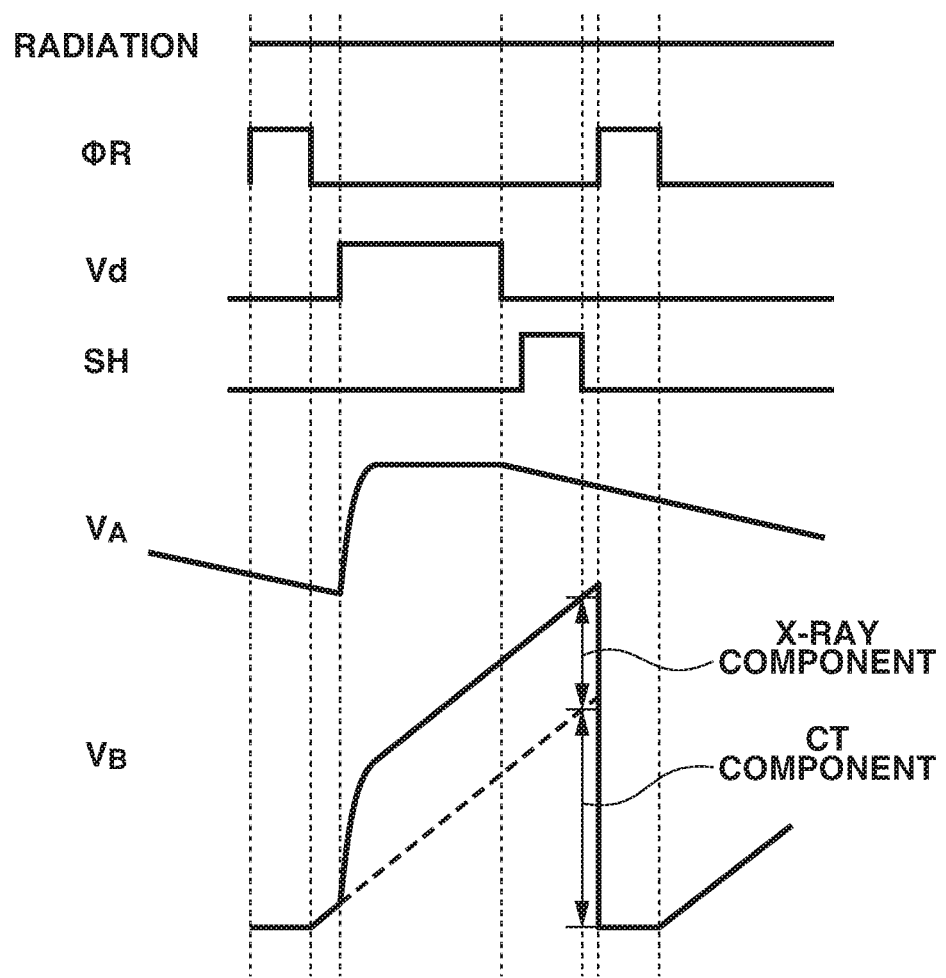
FIG. 7 is a timing chart illustrating a cause of generation of a crosstalk.
Figure 8:
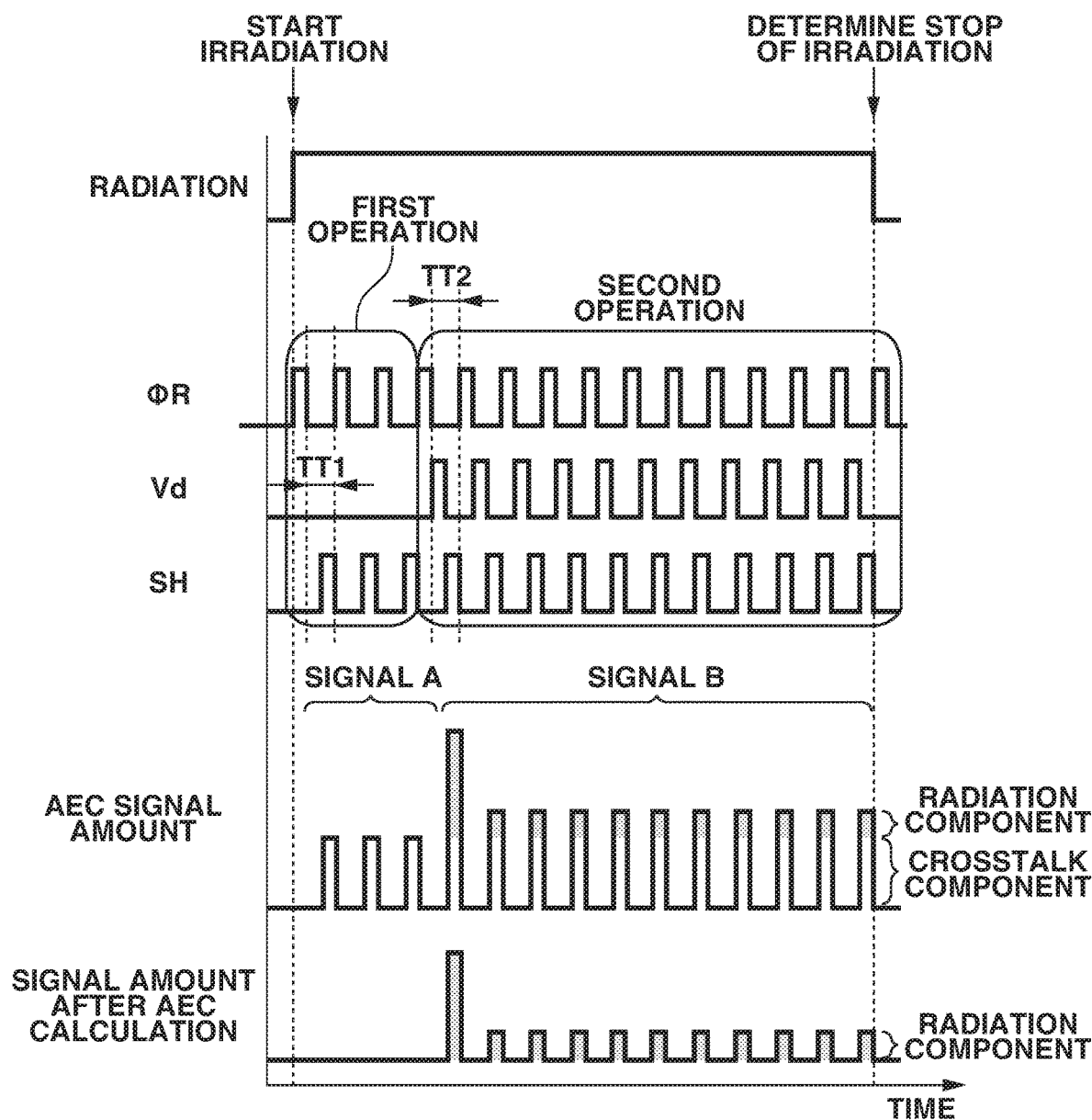
FIG. 8 is a timing chart illustrating the operation of the radiographic imaging apparatus according to the first exemplary embodiment.

Specific examples of a configuration and an operation of the readout unit 140 will be provided with reference to FIGS. 6 to 8. FIG. 6 illustrates the example of the configuration of the readout unit 140. FIG. 7 illustrates a mechanism by which a crosstalk occurs. FIG. 8 illustrates an example of the operation of the radiographic imaging apparatus 200 according to the present exemplary embodiment.

The detection unit 142 of the readout unit 140 includes an amplification circuit AMP, a holding capacitor HC, and a sampling switch SW. The amplification circuit AMP includes a differential amplifier DA, which includes a first input terminal, a second input terminal, and an output terminal, and a feedback capacitor Cf and a reset switch (reset unit) RS provided in parallel between this first input terminal and the output terminal. The detection signal line 125 is connected to this first input terminal, and a reference potential REF is supplied to this second terminal. The sampling switch SW is disposed between the output terminal of the differential amplifier DA (the amplification circuit AMP) and the holding capacitor HC. The first electrode 151 of the detection pixel 121 has a potential VA, and the output terminal of the differential amplifier DA (the amplification circuit AMP) has a potential VB. In other words, the sampling switch SW and the holding capacitor HC function as a sample-and-hold circuit that samples and holds the signal appearing in the detection signal line 125. A driving signal Vd illustrated in FIGS. 7 and 8 is the signal applied to the driving line 124. Further, when a reset signal ΦR is switched to the high level, the reset switch RS is caused to be in the conductive state and VB is reset to the reference potential REF.

During the irradiation by the radiation (the time period T2 illustrated in FIG. 3), the potential of the first electrode 151 of the imaging pixel 101 changes. According thereto, the potential of the detection signal line 125 changes due to the crosstalk via the parasitic capacitance between the first electrode 151 and the detection signal line 125. Therefore, as exemplified in FIG. 7, the potential VB of the output terminal of the differential amplifier DA (the amplification circuit AMP) also changes. In FIG. 7, a "crosstalk component" indicates the change in VB corresponding to the change in the potential of the detection signal line 125 due to the crosstalk. Further, a "radiation component" indicates the change in VB corresponding to the change in the potential of the detection signal line 125 when the second switch 123 is caused to be in the conductive state (i.e., the charge accumulated in the second conversion element 122). The signal accumulated in the holding capacitor HC by switching a sampling signal SH to the high level and causing the sampling switch SW to be in the conductive state intrinsically contains the "crosstalk component" and the "radiation component". Therefore, the "crosstalk" component should be removed to correctly acquire the signal.

In the following description, the operation of the present exemplary embodiment will be described with reference to FIG. 8. FIG. 8 illustrates only a portion corresponding to the time period T2 illustrated in FIG. 3 for the purpose of simplification. First, the reset signal ΦR is switched to the high level, and the reset switch RS is caused to be in the conductive state. By this operation, VB is reset to the reference potential REF. From the moment that the reset signal ΦR is switched to the low level and the reset switch RS is caused to be in the non-conductive state, VB starts changing due to the crosstalk. Next, at an initial stage of the irradiation, the sampling signal SH is switched from the low level to the high level and then switched to the low level again with the conduction of the second switch element 123 blocked and the potential of the driving line 124 kept at the low level. By this operation, the crosstalk component is sampled by the holding capacitor HC and the sampling switch SW. A first operation, which is a pair of these resetting and sampling, is performed once or repeated a plurality of times, by which a signal of the crosstalk component is acquired once or a plurality of times. The signal processing unit 224 acquires or calculates a "first signal A" of the crosstalk component per unit time in a pertinent imaging with use of the one or more signals acquired by the first operation during a time period TT1.

Next, after the reset signal ΦR is switched to the high level and the reset switch RS is caused to be in the conductive state, the reset signal ΦR is switched to the low level and the reset switch RS is caused to be in the non-conductive state. Then, a signal appearing in the detection signal line 125 after at least the second switch element 123 is caused to be in the conductive state is sampled. A second operation, which is a pair of the resetting and the sampling according to the second switch element 123 being caused to be in the conductive state during a time period TT2, is repeated. By the second operation, the signal processing unit 224 acquires a "second signal B" containing a signal of the radiation component accumulated in the second conversion element 122 due to the irradiation and a signal of the crosstalk component. Next, the signal processing unit 224 performs signal processing for outputting the information indicating the irradiation of the radiographic imaging apparatus 200 by the radiation based on the first signal A and the second signal B. More specifically, the signal processing unit 224 becomes able to make a correction for removing the "crosstalk component" from the "second signal B" by performing subtraction processing on the "first signal A" and the "second signal B".

In the present exemplary embodiment, before the second operation of acquiring the second signal B containing the radiation component and the crosstalk component to detect the radiation dose is performed a plurality of times consecutively, the first signal A containing only the crosstalk component without containing the radiation component is acquired. Accordingly, the second operation can be repeatedly performed alone without the first operation performed between the consecutive second operations performed the plurality of times. Therefore, the present exemplary embodiment allows the radiographic imaging apparatus 200 to detect the radiation dose without reducing a temporal resolution of the detection of the radiation dose. An amount of the crosstalk generated in each detection signal line 125 changes for each subject and each imaging, and therefore it is desirable to perform the first operation for each imaging.

Figure 9:
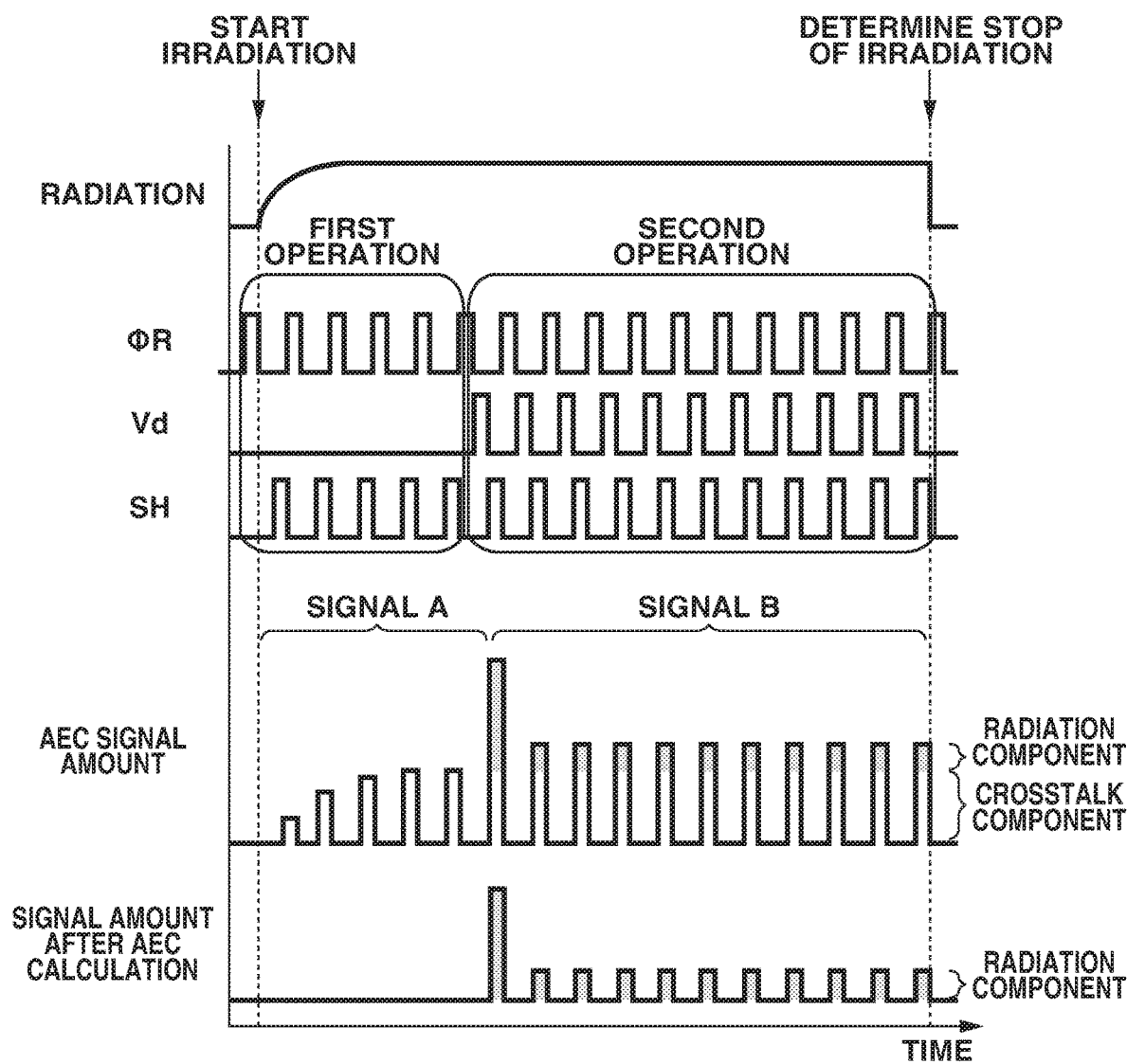
FIG. 9 is a timing chart illustrating an exemplary modification of the operation of the radiographic imaging apparatus according to the first exemplary embodiment.

Depending on the radiation source, an irradiation intensity may be unstable at an initial stage of the start of the radiation and be gradually stabilized into an intended intensity. In such a case, the crosstalk changes according to the irradiation intensity of the radiation. It is desirable to perform the first operation of acquiring the crosstalk amount with the radiation dose stabilized, so that it is desirable to continue the first operation until the irradiation intensity is stabilized as illustrated in FIG. 9. Using the signal A of the crosstalk component after the irradiation intensity is stabilized for the correction of the second signal B acquired by the second operation allows the radiographic imaging apparatus 200 to detect the radiation component alone accurately. Because the radiation intensity and the crosstalk amount are in proportion to each other, whether the irradiation intensity of the radiation is stabilized can be determined according to whether the signal amount acquired by the first operation is stabilized.

Further, in the example described so far, the time period TT1 of the first operation and the time period TT2 of the second operation have been described as having the same time lengths as each other by way of example. Accordingly, respective sampling intervals are set to the same time lengths between the first operation and the second operation, and the crosstalk component is kept approximately constant between the respective time periods as long as the irradiation amount per unit time is stabilized. This consistency allows the radiographic imaging apparatus 200 to accurately make the correction by the subtraction processing on the first signal A and the second signal B. Here, the sampling interval refers to an interval between the individual operations of the first operation performed the plurality of times or the second operation performed the plurality of times. Further, by controlling the first operation and the second operation in such a manner that the same operations are performed in every process between the first operation and the second operation except for the operation of the second switch element 123, a difference in the signal due to the difference in the operation can be minimized, and hence the correction accuracy can be improved.

Figure 10:
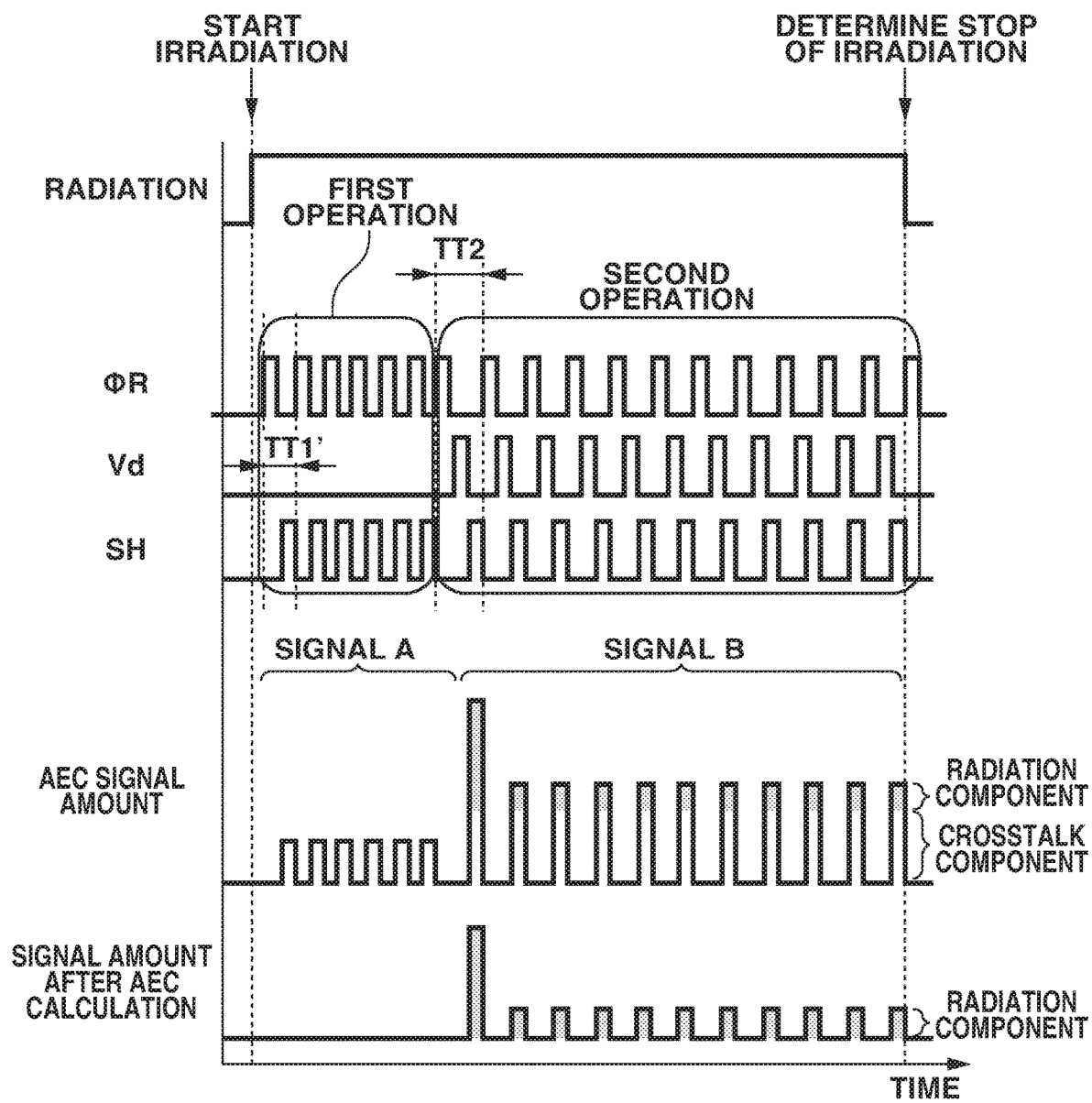
FIG. 10 is a timing chart illustrating an exemplary modification of the operation of the radiographic imaging apparatus according to the first exemplary embodiment.

However, even when the respective sampling time periods are different between the first operation and the second operation as illustrated in FIG. 10, the correction is possible. For example, in a case where a time period TT1' (and the sampling interval according thereto) of the first operation is half the time period TT2 (and the sampling interval according thereto) of the second operation, the crosstalk component acquired by the second operation is approximately twice the crosstalk component acquired by the first operation. Therefore, correcting the signal acquired by the second operation based on a value twice the signal acquired by the first operation according to a ratio of the respective time periods allows the radiographic imaging apparatus 200 to accurately correct the crosstalk. In this manner, the radiographic imaging apparatus 200 can accurately correct the crosstalk by making the correction according to the ratio of the time periods of the individual operations. Reducing the sampling interval of the first operation allows the radiographic imaging apparatus 200 to acquire the crosstalk amount, which is the correction value, in a short time period, thereby bringing about a merit of facilitating a swift transition to the second operation, which monitors the detection of the radiation dose.

Further, as a method for calculating the correction value in the case where the sampling intervals are different between the first operation and the second operation, the radiographic imaging apparatus 200 may acquire data for calibration for the first operation and the second operation in advance and use it for the correction. For example, the radiographic imaging apparatus 200 acquires in advance a difference in the signal amount when the radiographic imaging apparatus 200 is irradiated with the same radiation between the first operation and the second operation having the different sampling intervals from each other. The radiographic imaging apparatus 200 uses a difference in the crosstalk amount between the first operation and the second operation based on a ratio of these signals for the correction of the signal acquired by the second operation as the calibration data. Even when a difference is generated in the crosstalk amount between the first operation and the second operation due to a cause other the sampling interval, confirming the difference between these signal amounts in advance by actual measurement and correcting the difference allows the radiographic imaging apparatus 200 to accurately make the correction.

Further, regarding the first operation, the radiographic imaging apparatus 200 is required to start monitoring the irradiation amount quickly. Thus, it is desirable to acquire the signal thereof at the time of the initial stage of the irradiation. However, the effect of the present exemplary embodiment can be acquired by not only a configuration in which the first operation is performed at the initial stage of the irradiation but also a configuration in which the first operation is performed after the irradiation amount is stabilized and then transition is made to the second operation.

Figure 11:
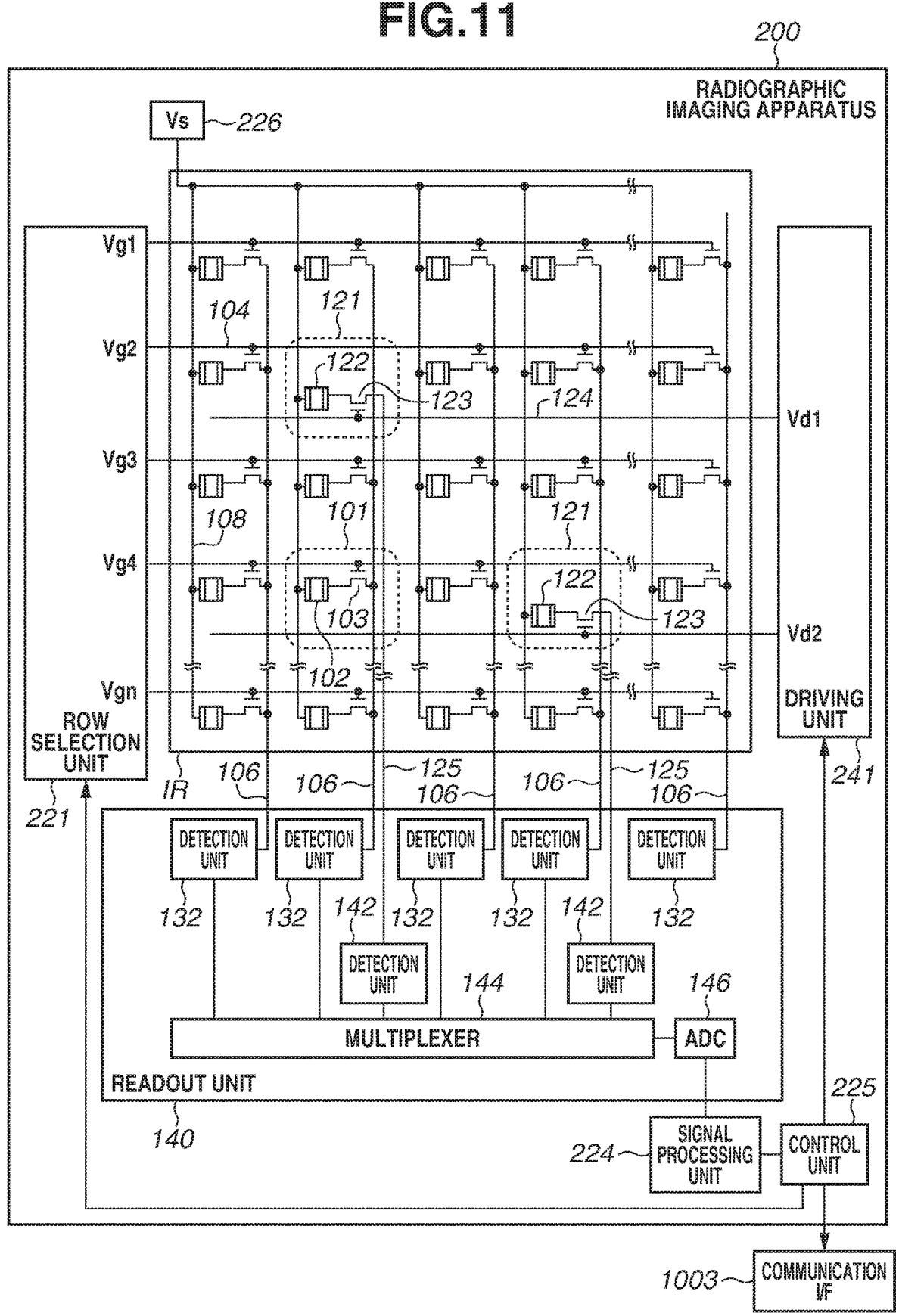
FIG. 11 is a diagram illustrating a configuration of an exemplary modification of the radiographic imaging apparatus according to the first exemplary embodiment.

As illustrated in FIG. 1, in the present exemplary embodiment, the signal from the imaging pixel 101 and the signal from the detection pixel 121 are read out by the different readout units 130 and 140. However, the disclosure is not limited thereto, and these signals may be read out by the common readout unit 140 as exemplified in FIG. 11.

Figure 12:
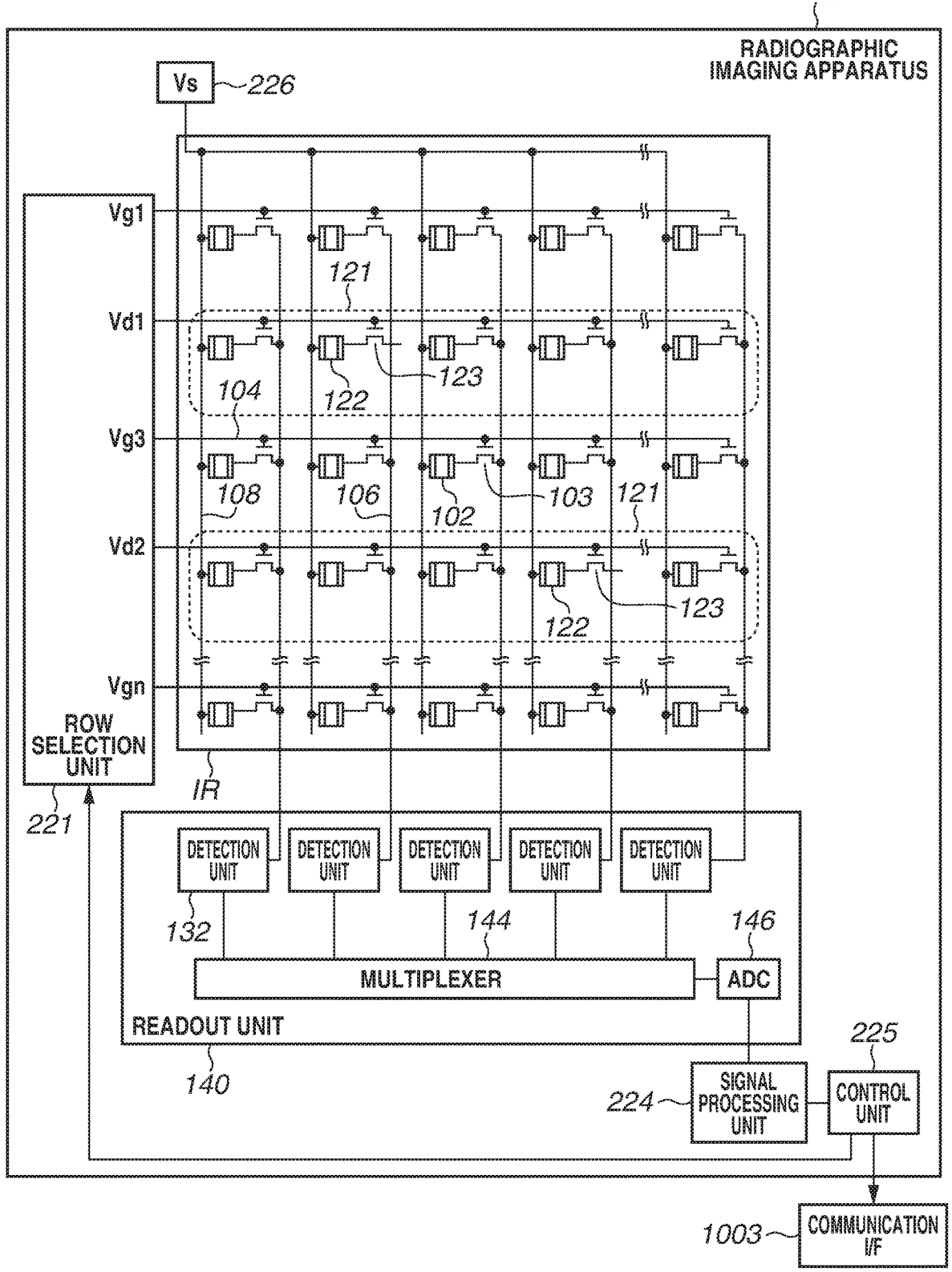
FIG. 12 is a diagram illustrating a configuration of an exemplary modification of the radiographic imaging apparatus according to the first exemplary embodiment.

Further, in the present exemplary embodiment, the radiographic imaging apparatus 200 has been described as including the detection pixel 121 connected to the dedicated detection signal line 125 and the dedicated detection driving line 124 by way of example, but the disclosure is not limited thereto. For example, the radiographic imaging apparatus 200 may be configured to employ a pixel array in which all of the pixels are configured similarly to one another and use a part of rows as the detection pixel 121 as exemplified in FIG. 12.

Next, a second exemplary embodiment will be described with reference to FIG. 13. Features that will not be described as the second exemplary embodiment can comply with the first exemplary embodiment.

In the first exemplary embodiment, the radiographic imaging apparatus 200 has been described as providing the time period during which the crosstalk is acquired by the first operation only in the initial stage of the start of the irradiation by way of example, but the second exemplary embodiment indicates an example that has this time period at a plurality of timings besides the initial stage of the start of the irradiation.

Figure 13:
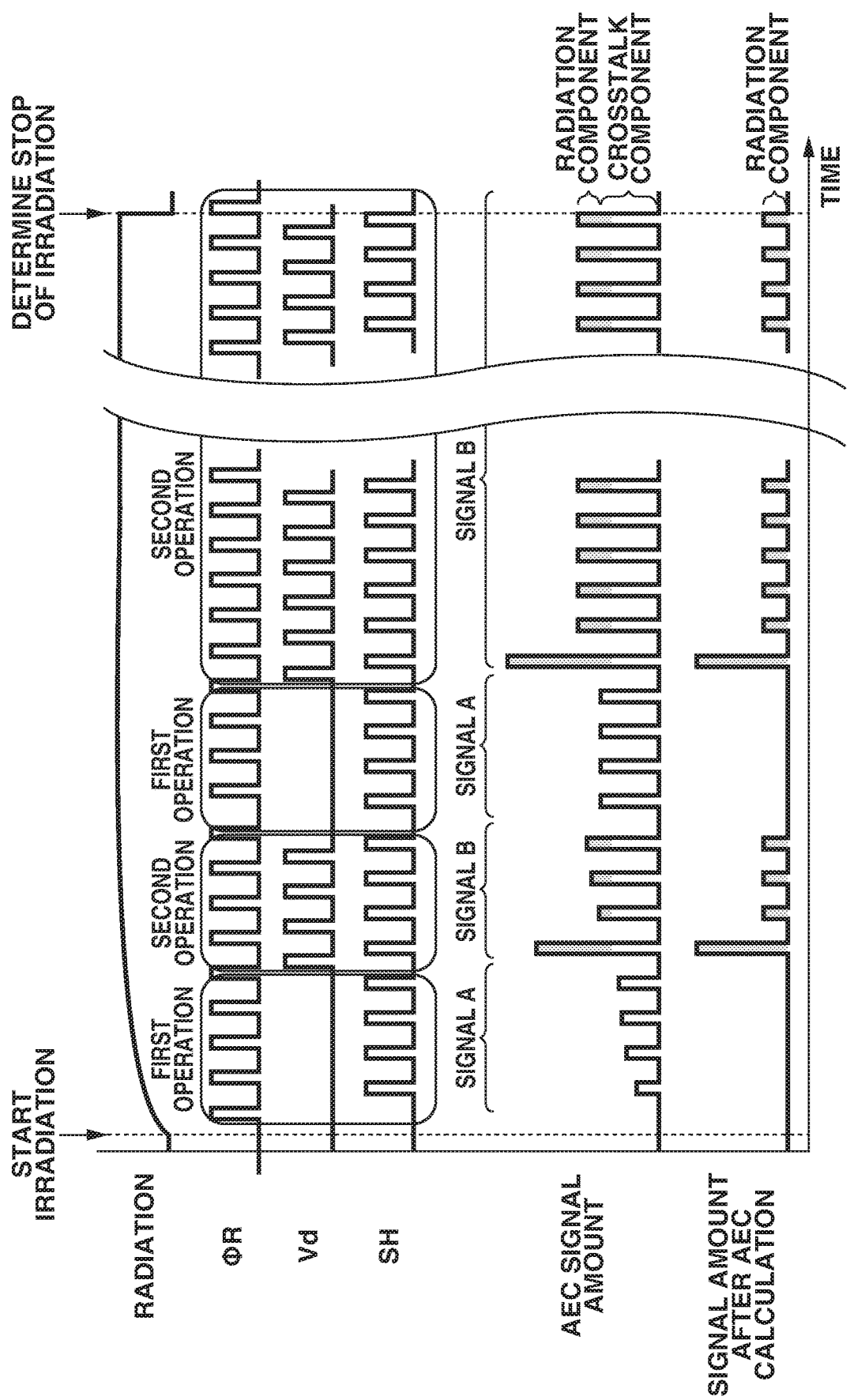
FIG. 13 is a timing chart illustrating an operation of a radiographic imaging apparatus according to a second exemplary embodiment.

As illustrated in FIG. 13, for example, in such a case that the irradiation amount changes during the irradiation like when irradiation with radiation at a low intensity is performed for a long time period, a change occurs in the "second signal B" containing the "radiation component" and the "crosstalk component". Therefore, if the change occurs in the "second signal B", the radiographic imaging apparatus 200 returns to the first operation, and reacquires the "first signal A" containing the crosstalk component. After that, the radiographic imaging apparatus 200 transitions to the second operation again, and corrects the second signal B by performing the subtraction processing based on the "first signal A" containing the reacquired crosstalk component, thereby acquiring the signal with the crosstalk component removed from the second signal B.

Such an operation allows the radiographic imaging apparatus 200 to correctly extract the signal even when the irradiation amount changes during the irradiation. Further, the radiographic imaging apparatus 200 may perform such control that the radiographic imaging apparatus 200 periodically returns from the second operation to the first operation, such as periodically updating the crosstalk component.

Figure 14:
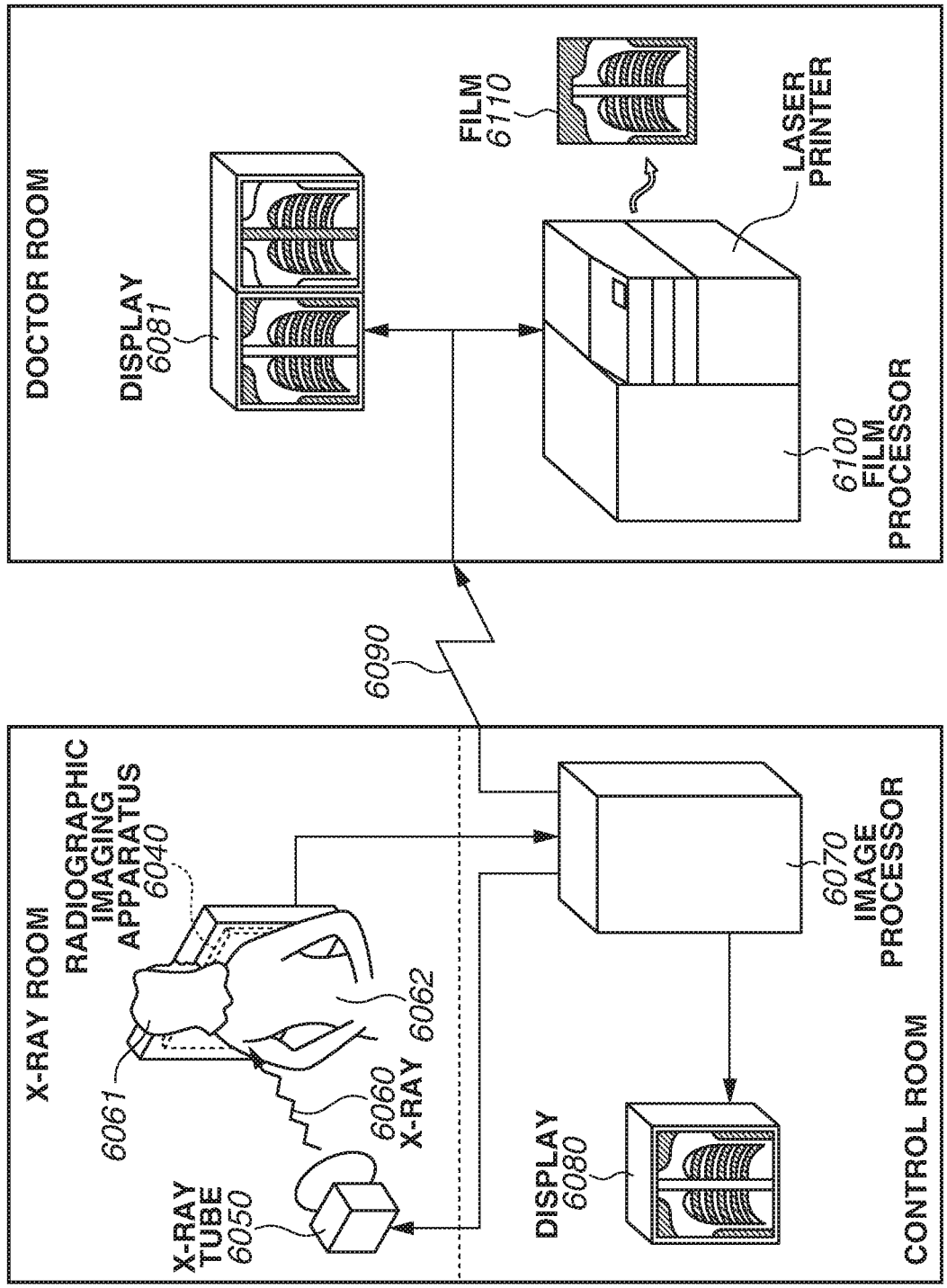
FIG. 14 is a diagram illustrating an example of a configuration of a radiation detection system.

In the following description, an example in which the radiographic imaging apparatus 200 is applied to a radiation detection system will be described with reference to FIG. 14. An X-ray 6060 generated in an X-ray tube 6050, which is a radiation source, is transmitted through a chest portion 6062 of a patient or subject 6061, and is incident on a radiographic imaging apparatus 6040 represented by the above-described radiographic imaging apparatus 200. The X-ray 6060, which is this incident radiation, contains information of an inside of a body of the subject 6061. A scintillator (not illustrated) of the radiographic imaging apparatus 6040 emits light in response to the incidence of the X-ray 6060, and this is photoelectrically converted by a photoelectric conversion element of the radiographic imaging apparatus 6040, by which electric information is acquired. This information is converted into a digital signal and subjected to image processing by an image processor 6070 serving as a signal processing unit, and can be observed on a display 6080 serving as a display unit in a control room.

Further, this information can be transferred to a remote location by a transmission processing unit such as a telephone line 6090 and can be displayed on a display 6081 serving as the display unit or stored in a recording unit such as an optical disk in, for example, a doctor room placed at another location, thereby allowing even a doctor at the remote location to make a diagnosis. Further, this information can also be recorded on a film 6110 serving as a recording medium by a film processor 6100 serving as the recording unit.

OTHER EMBODIMENTS

Embodiment(s) of the disclosure can also be realized by a computer of a system or apparatus that reads out and executes computer executable instructions (e.g., one or more programs) recorded on a storage medium (which may also be referred to more fully as a 'non-transitory computer-readable storage medium') to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s). The computer may comprise one or more processors (e.g., central processing unit (CPU), micro processing unit (MPU)) and may include a network of separate computers or separate processors to read out and execute the computer executable instructions. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the disclosure has been described with reference to exemplary embodiments, it is to be understood that the disclosure is not limited to the disclosed exemplary embodiments. The scope of the following claims is to be accorded the broadest interpretation so as to encompass all such modifications and equivalent structures and functions.

This application claims the benefit of Japanese Patent Application No. 2016-228061, filed Nov. 24, 2016, which is hereby incorporated by reference herein in its entirety.

What is claimed is:

1. A radiographic imaging apparatus comprising:
  a pixel including a conversion element configured to convert radiation generated by a radiation source into an electric signal and a switch configured to connect the conversion element to a signal line;
  a readout unit that includes a reset unit configured to reset a potential of the signal line, wherein, during a time period when the radiation source generates radiation, the readout unit is configured to perform a first operation and a second operation, and perform the first operation before performing the second operation a plurality of times consecutively;
  wherein the first operation is a pair of an operation of resetting the potential of the signal line by the reset unit and a subsequent operation of reading out the signal appearing in the signal line when the switch is not in the conductive state, and
  wherein the second operation is a pair of an operation of resetting the potential of the signal line by the reset unit and a subsequent operation of reading out the signal appearing in the signal line when the switch is in the conductive state; and
  a signal processing unit configured to perform signal processing for outputting information indicating irradiation of the radiographic imaging apparatus by the radiation based on the first signal and the second signal.

2. The radiographic imaging apparatus according to claim 1, wherein the signal processing unit performs subtraction processing on the first signal and the second signal.

3. The radiographic imaging apparatus according to claim 1, wherein the signal processing unit performs the signal processing with use of the first signal read out by the readout unit after an irradiation intensity of the radiation with which the radiographic imaging apparatus is irradiated is stabilized.

4. The radiographic imaging apparatus according to claim 1, wherein, after returning to the first operation to reacquire the first signal after the second operation, the readout unit retransitions to the second operation performed the plurality of times.

5. The radiographic imaging apparatus according to claim 1, wherein the readout unit includes a differential amplifier including a first input terminal to which an electric signal is supplied via the signal line, a second input terminal to which a reference potential is supplied, and an output terminal, and
  wherein the reset unit includes a switch connecting the first input terminal and the output terminal to each other.

6. The radiographic imaging apparatus according to claim 1, wherein the readout unit includes a sample-and-hold circuit configured to sample and hold the signal appearing in the signal line.

7. The radiographic imaging apparatus according to claim 1, wherein a time period of the first operation during which the first operation is performed and a time period of the second operation during which the second operation is performed have same time lengths as each other.

8. The radiographic imaging apparatus according to claim 1, wherein, if a time period of the first operation during which the first operation is performed and a time period of the second operation during which the second operation is performed have different time lengths from each other, the signal processing unit performs the signal processing with use of a ratio of the time lengths of the time period of the first operation and the time period of the second operation.

9. The radiographic imaging apparatus according to claim 1, wherein the pixel is a pixel for monitoring the irradiation by the radiation,
  wherein the radiographic imaging apparatus includes, in addition to the pixel, a plurality of imaging pixels for capturing a radiographic image, and
  wherein the pixel is disposed in a same column as a part of the plurality of imaging pixels.

10. The radiographic imaging apparatus according to claim 9, wherein signals of the plurality of imaging pixels are read out via a different signal line from the signal line.

11. The radiographic imaging apparatus according to claim 1, wherein the pixel is a pixel for capturing a radiographic image.

12. A radiographic imaging system comprising:
  a radiation source configured to generate radiation; and
  the radiographic imaging apparatus according to claim 1.

13. The radiographic imaging system according to claim 12, wherein the radiographic imaging apparatus further includes a control unit configured to control the readout unit based on the information from the signal processing unit, and
  wherein the control unit outputs a signal for stopping emission of the radiation by the radiation source based on the information from the signal processing unit.

* * * * *